(12) United States Patent
Nakamura

(10) Patent No.: US 9,445,709 B2
(45) Date of Patent: Sep. 20, 2016

(54) IMAGING UNIT AND IMAGING SYSTEM

(71) Applicant: OLYMPUS CORPORATION, Tokyo (JP)

(72) Inventor: Mikio Nakamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 264 days.

(21) Appl. No.: 14/327,653

(22) Filed: Jul. 10, 2014

(65) Prior Publication Data

US 2014/0320619 A1 Oct. 30, 2014

Related U.S. Application Data

(63) Continuation of application No. PCT/JP2013/050233, filed on Jan. 9, 2013.

(30) Foreign Application Priority Data

Jan. 16, 2012 (JP) .................................. 2012-006335

(51) Int. Cl.
*A61B 1/00* (2006.01)
*H04N 7/18* (2006.01)
(Continued)

(52) U.S. Cl.
CPC ....... *A61B 1/00006* (2013.01); *A61B 1/00013* (2013.01); *A61B 1/00018* (2013.01); *A61B 1/00036* (2013.01); *A61B 1/00057* (2013.01); *A61B 1/042* (2013.01); *A61B 1/045* (2013.01);
(Continued)

(58) Field of Classification Search
CPC ..................... A61B 1/00006; A61B 1/00011

USPC ........................................................... 348/65
See application file for complete search history.

(56) References Cited

U.S. PATENT DOCUMENTS

2003/0234776 A1 12/2003 Konishi
2007/0232860 A1 10/2007 Kubo et al.
(Continued)

FOREIGN PATENT DOCUMENTS

EP          1 982 639 A2   10/2008
JP       2000-341175 A     12/2000
(Continued)

OTHER PUBLICATIONS

International Search Report dated Apr. 16, 2013 issued in PCT/JP2013/050233.
(Continued)

*Primary Examiner* — Jeffery Williams
(74) *Attorney, Agent, or Firm* — Scully, Scott, Murphy & Presser, PC

(57) ABSTRACT

An imaging unit includes: an imager that receives and photoelectrically converts light from a target to be captured; a branching unit that branches a signal from the imager into two signals; a first converter into which one of the two signals is input to convert the input signal into an optical signal; a second converter into which the other of the two signals is input to convert the input signal into an electric signal; a first output unit that outputs the optical signal; a second output unit that outputs the electric signal; a detector that detects a unit connected to the imaging unit; and a controller that causes the first output unit to output the optical signal if the unit detected by the detector is the control unit, and causes the second output unit to output the electric signal if the unit detected by the detector is the inspection unit.

5 Claims, 4 Drawing Sheets

(51) Int. Cl.
*A61B 1/04* (2006.01)
*A61B 1/045* (2006.01)
*H04N 5/225* (2006.01)

(52) U.S. Cl.
CPC ...... *H04N 7/183* (2013.01); *H04N 2005/2255* (2013.01)

(56) References Cited

U.S. PATENT DOCUMENTS

2010/0124422 A1* 5/2010 Ishida .................. H04B 10/564
398/182
2013/0096380 A1  4/2013 Matsuzawa et al.

FOREIGN PATENT DOCUMENTS

| | | |
|---|---|---|
| JP | 2006-026133 A | 2/2006 |
| JP | 2007-260066 A | 10/2007 |
| JP | 2009-056240 A | 3/2009 |
| JP | 2010-051503 A | 3/2010 |
| WO | WO 2012/046856 A1 | 4/2012 |

OTHER PUBLICATIONS

Extended Supplementary European Search Report dated Sep. 4, 2015 from related European Application No. 13 73 8302.2.

* cited by examiner

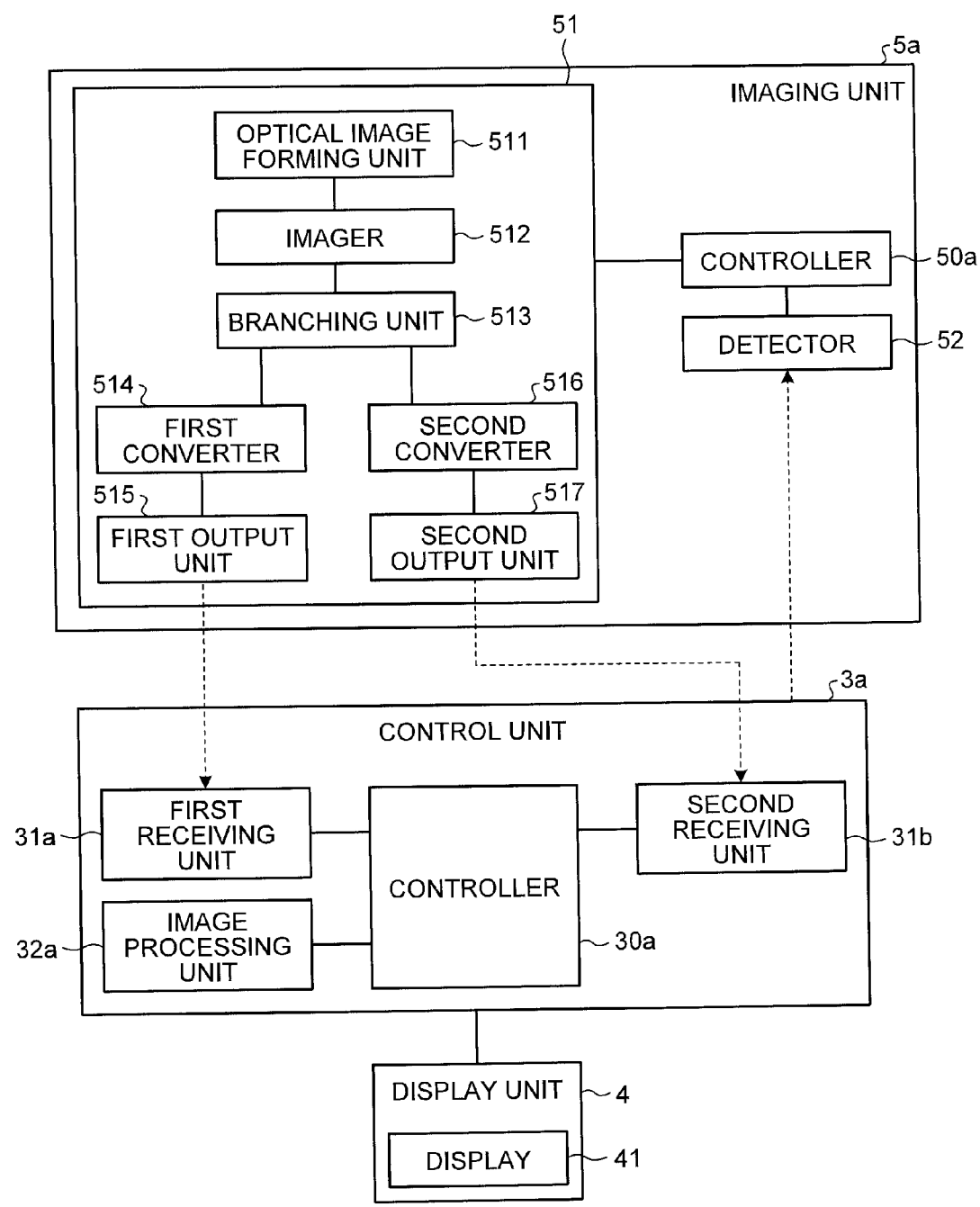

IMAGING UNIT AND IMAGING SYSTEM

CROSS-REFERENCE TO RELATED APPLICATIONS

This application is a continuation of PCT international application Ser. No. PCT/JP2013/050233 filed on Jan. 9, 2013 which designates the United States, incorporated herein by reference, and which claims the benefit of priority from Japanese Patent Application No. 2012-006335, filed on Jan. 16, 2012, incorporated herein by reference.

BACKGROUND

1. Technical Field

The disclosure relates to an imaging unit having an imaging element and an optical member and to an imaging system.

2. Related Art

Conventionally, electronic imaging systems corresponding to various types have appeared on the market, like digital cameras and digital video cameras, as well as portable telephones having imaging functions and endoscope systems for observing insides of organs of subjects. Of these, an endoscope system includes: an endoscope apparatus having an imaging unit that captures an image of inside of an organ of a subject; and a control unit that controls this endoscope apparatus. The imaging unit is built-in, with an imaging element mounted on a distal end portion of an elongated insertion tool having flexibility. By inserting this insertion tool inside a body cavity, observation or the like of a site to be tested becomes possible.

The imaging unit has the imaging element such as a CCD image sensor or a CMOS image sensor mounted thereon, forms an optical image of the subject on a light receiving unit of the imaging element by an optical system such as a lens, and performs a photoelectric conversion process on an image signal of this optical image to thereby capture image data of the subject.

In recent years, for smooth diagnosis and treatment, increase in definition of in-vivo images is demanded. Under such situations, in order to transmit an image signal having a large amount of information corresponding to the increase in definition, an endoscope system has been proposed, which converts an electric signal into an optical signal, and transmits this converted optical signal to a signal processing apparatus by using an optical fiber cable (for example, see Japanese Laid-open Patent Publication No. 2007-260066).

SUMMARY

In some embodiments, an imaging unit is communicatively connected to a control unit for operation control, performs image capturing of a target to be captured under control of the control unit, and is also communicatively connected to an inspection unit for conduction inspection and subjected to the conduction inspection. The imaging unit includes: an imager that has an imaging element configured to receive and photoelectrically convert light from the target to be captured; a branching unit configured to branch a signal including image information input from the imager into two signals; a first converter into which one of the two signals branched by the branching unit is input and which is configured to perform a conversion process of converting the input signal into an optical signal; a second converter into which the other of the two signals branched by the branching unit is input and which is configured to perform a conversion process of converting the input signal into an electric signal; a first output unit configured to output the optical signal converted by the first converter to outside; a second output unit configured to output the electric signal converted by the second converter to outside; a detector configured to detect a unit connected to the imaging unit; and a controller configured to cause the first output unit to output the optical signal if the unit detected by the detector is the control unit, and configured to cause the second output unit to output the electric signal if the unit detected by the detector is the inspection unit.

In some embodiments, an imaging system includes: the above-described imaging unit; the control unit that has a first receiving unit communicatively connected to the first output unit and configured to receive a signal from the imaging unit, and has a first image processing unit configured to generate image information based on the signal received by the first receiving unit; the inspection unit that has a second receiving unit communicatively connected to the second output unit and configured to receive a signal from the imaging unit, and has a second image processing unit configured to generate image information based on the signal received by the second receiving unit; and a display configured to perform image display, based on the image information generated by the first image processing unit or the second image processing unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 4 is a block diagram illustrating a control unit, and an imaging unit mounted on a distal end portion of an endoscope apparatus, of an endoscope system according to a modified example of the embodiment of the present invention.

DETAILED DESCRIPTION

Hereinafter, modes for carrying out the present invention will be described in detail with reference to the drawings. The present invention is not limited by the following embodiment. Further, each drawing referred to in the following description schematically illustrates shapes, sizes, and positional relations merely to an extent that allows contents of the present invention to be understood. That is, the present invention is not limited only to the shapes, sizes, and positional relations exemplified in each drawing. In the following description, an endoscope system will be described as an example of an imaging system.

Figure 1:
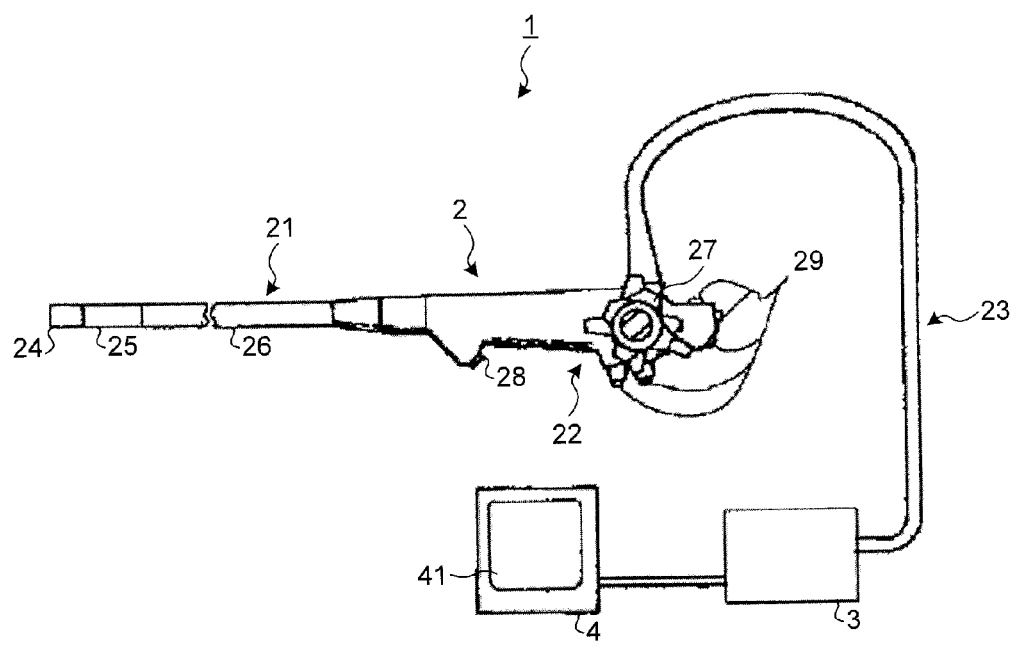
FIG. 1 is a schematic diagram illustrating an overall configuration of an endoscope system according to an embodiment of the present invention.

First, an endoscope system according to an embodiment will be described. FIG. 1 is a schematic diagram illustrating an overall configuration of an endoscope system 1 according to this embodiment. As illustrated in FIG. 1, an endoscope system 1 according to the embodiment includes: an endoscope apparatus 2, which has an imaging unit that captures an image of inside of an organ of a subject; a control unit 3 for operation control of controlling this endoscope apparatus 2; and a display unit 4, which is connected to the control unit 3 and displays a captured image or the like captured by the endoscope apparatus 2.

The endoscope apparatus 2 includes: an insertion unit 21, which is elongated; an operating unit 22, which is at a proximal end side of this insertion unit 21 and held by an endoscope apparatus operator; and a universal cord 23, which extends from a side portion of this operating unit 22 and is flexible. The universal cord 23 has an optical fiber cable, an electric cable, and the like therein.

The insertion unit 21 includes a distal end portion 24 which has an imaging unit therein that has an imaging element such as a CCD, a bending portion 25 which has a plurality of bending pieces and is freely bendable, and a flexible tube portion 26 which is provided at a proximal end side of this bending portion 25, is long, and has flexibility. The imaging unit is connected communicatively to the control unit 3 for the operation control and performs image capturing of a target to be captured under the control of the control unit 3, and is also connected communicatively to an inspection unit 6 (see FIG. 3) for conduction inspection and subjected to the conduction inspection.

At an end portion at a control unit 3 side of the universal code 23: a light guide connecter connected freely detachably from a light source device; an electric contact portion for transmitting an electric signal of a subject image photoelectrically converted by the CCD or the like; an air supply mouthpiece for sending air to a nozzle of the distal end portion 24; and the like, are provided (not illustrated). The light source device has a halogen lamp and the like therein and supplies, as illumination light, light from the halogen lamp to the endoscope apparatus 2 connected via the light guide connector.

The operating unit 22 includes a bending knob 27 that bends the bending portion 25 in a vertical direction and a horizontal direction, a treatment tool insertion portion 28 through which a treatment tool such as biopsy forceps or a laser probe is inserted in a body cavity, and a plurality of switches 29 that execute operations of peripheral devices, such as a signal processing apparatus and a control device, or air supply, water supply, and gas supply means. The endoscope apparatus 2, in which the treatment tool has been inserted in the treatment tool insertion opening of the treatment tool insertion portion 28, causes a distal end treatment portion of the treatment tool to protrude via a treatment tool insertion channel provided inside thereof, and performs a biopsy or the like of collecting affected tissue by the biopsy forceps, for example.

The control unit 3 supplies electric power to the imaging element, the electric signal photoelectrically converted is input to the control unit 3 from the imaging element, the control unit 3 processes the electric signal captured by the imaging element, causes the display unit 4 connected to display the image, and performs control such as gain adjustment of the imaging element and outputting of a drive signal that drives the imaging element.

The display unit 4 has a display 41 that is caused to display, under the control of the control unit 3, the captured image captured by the imaging element.

Figure 2:
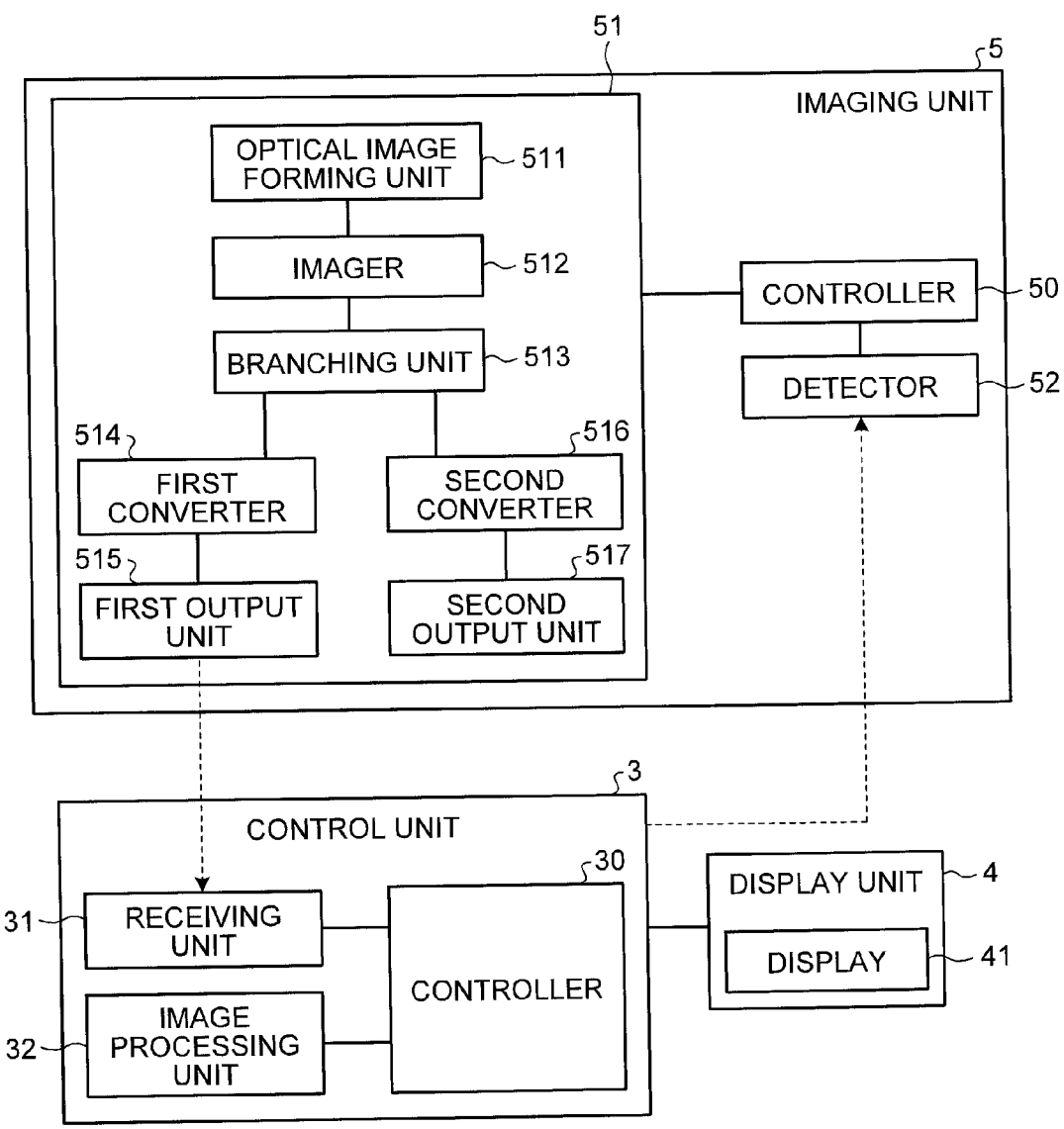
FIG. 2 is a block diagram illustrating a control unit, and an imaging unit mounted on a distal end portion of an endoscope apparatus, of the endoscope system according to the embodiment of the present invention.

Next, a configuration of an imaging unit mounted on the distal end portion 24 of the endoscope apparatus 2 and a configuration of a control unit will be described. FIG. 2 is a block diagram illustrating the control unit 3, and the imaging unit 5 mounted on the distal end portion 24 of the endoscope apparatus 2, of the endoscope system 1 according to this embodiment.

The control unit 3 has: a controller 30 that controls the whole endoscope system 1 including the imaging unit 5; a receiving unit 31 (first receiving unit) that receives from the imaging unit 5 an optical signal output from the imaging unit 5; an image processing unit 32 (first image processing unit) that processes (conversion process into an electric signal) the optical signal received by the receiving unit 31 and generates image information of an image to be displayed by the display 41.

The imaging unit 5 includes a controller 50 that controls the whole imaging unit 5, an image acquiring unit 51 that acquires an image of the subject, and a detector 52 that detects another unit connected to the imaging unit 5.

The image acquiring unit 51 includes: an optical image forming unit 511 formed of a plurality of lenses; an imager 512, which has an imaging element that receives light from a target to be captured and photoelectrically converts the light; a branching unit 513 that branches a signal including image information input from the imager 512; a first converter 514 to which one signal of signals branched by the branching unit 513 is input and which performs a conversion process on this input signal; a first output unit 515 that outputs the signal converted by the first converter 514 to outside of the imaging unit 5; a second converter 516 to which the other signal of the signals branched by the branching unit 513 is input and which performs a conversion process on this input signal; and a second output unit 517 that outputs the signal converted by the second converter 516 to the outside of the imaging unit 5.

The optical image forming unit 511 has a plurality of lenses that condense light from outside. The plurality of lenses are assembled in a lens holder or the like so that respective centers thereof are positioned on the same axis, for example. The lens holder is formed, for example, of corrosion resistant steel, and at least an outer side thereof is shielded from light.

The imager 512 has an imaging element that receives and photoelectrically converts at least light from the target to be captured. A prism may be placed on the imaging element so that the imaging element receives light incident on and bent by the prism. The imaging element is a semiconductor element of a bare chip form exemplified by a CCD, a CMOS image sensor, or the like and has an imaging function of receiving light from a subject and capturing an image of the subject. In the imaging element, a light receiving unit, which receives the light from the subject and performs a photoelectrical conversion process on this received light, is formed on a top surface of a chip substrate thereof. When the imaging unit 5 is complete, the imaging element is arranged such that an optical axis of the lens of the optical image forming unit 511 and a light receiving unit surface thereof become approximately parallel to each other, for example.

The light receiving unit is realized by using: a group of pixels arranged in a predetermined shape, such as a lattice shape; a micro lens formed on the group of pixels for condensing light efficiently; and the like. A surface of the light receiving unit is rectangular shaped and the light receiving unit is formed at a predetermined position on the chip substrate of the imaging element.

The imager 512 generates an image signal of the subject based on the electric signal received and subjected to the photoelectric conversion process by the receiving unit of the imaging element, and outputs this generated image signal to the branching unit 513.

Under the control of the controller 50, the branching unit 513 branches the signal input from the imager 512 into two and makes an output to the first converter 514 and/or the second converter 516.

The first converter 514 converts the image signal, which is the electric signal input from the branching unit 513, into an optical signal. The first converter 514 has, for example, an E/O conversion module that converts the electric signal including the image signal into the optical signal. After converting the electric signal to the optical signal, the first converter 514 outputs it to the first output unit 515.

The second converter 516 converts the image signal, which is the electric signal input from the branching unit 513, into an electric signal of a mode that the second output unit 517 outputs. This conversion of the electric signal includes analog/digital conversion, adjustment of frequency characteristics, and the like. After converting the electric signal, the second converter 516 outputs it to the second output unit 517.

If an external unit is connected to the imaging unit 5, the detector 52 acquires information on the connected unit and outputs the acquired unit detection information to the controller 50. The receiving unit 31 of the control unit 3 is mechanically connected to any one of the first output unit 515 and second output unit 517 of the imaging unit 5. The detector 52 determines whether or not the control unit 3 has been connected, according to whether or not the optical fiber cable (universal cord 23) has been connected to the first output unit 515, for example.

In this embodiment, if the imaging unit 5 (endoscope apparatus 2) is connected to the control unit 3 as illustrated in FIG. 2, the imaging unit 5 and the control unit 3 are connected communicatively by the first output unit 515 and the receiving unit 31. When this is done, the detector 52 acquires information on the unit being connected and outputs detection information of the connected unit to the controller 50. The controller 50 controls the branching unit 513, the first output unit 515, and the second output unit 517, based on the unit detection information acquired from the detector 52.

Thereby, the control unit 3 receives the optical signal from the imaging unit 5, the optical signal including the image information and having been converted by the first converter 514, and thus transmission of an image signal having a large amount of information corresponding to increase in definition becomes possible between the control unit 3 and the imaging unit 5.

Based on the optical signal received by the receiving unit 31, the controller 30 causes the image processing unit 32 to process this optical signal and to generate image information, and causes, based on this image information, the display 41 of the display unit 4 to display an image. Thereby, an observer is able to check the image displayed by the display 41 to determine whether or not there is abnormality in the image acquired from the imaging unit 5.

Figure 3:
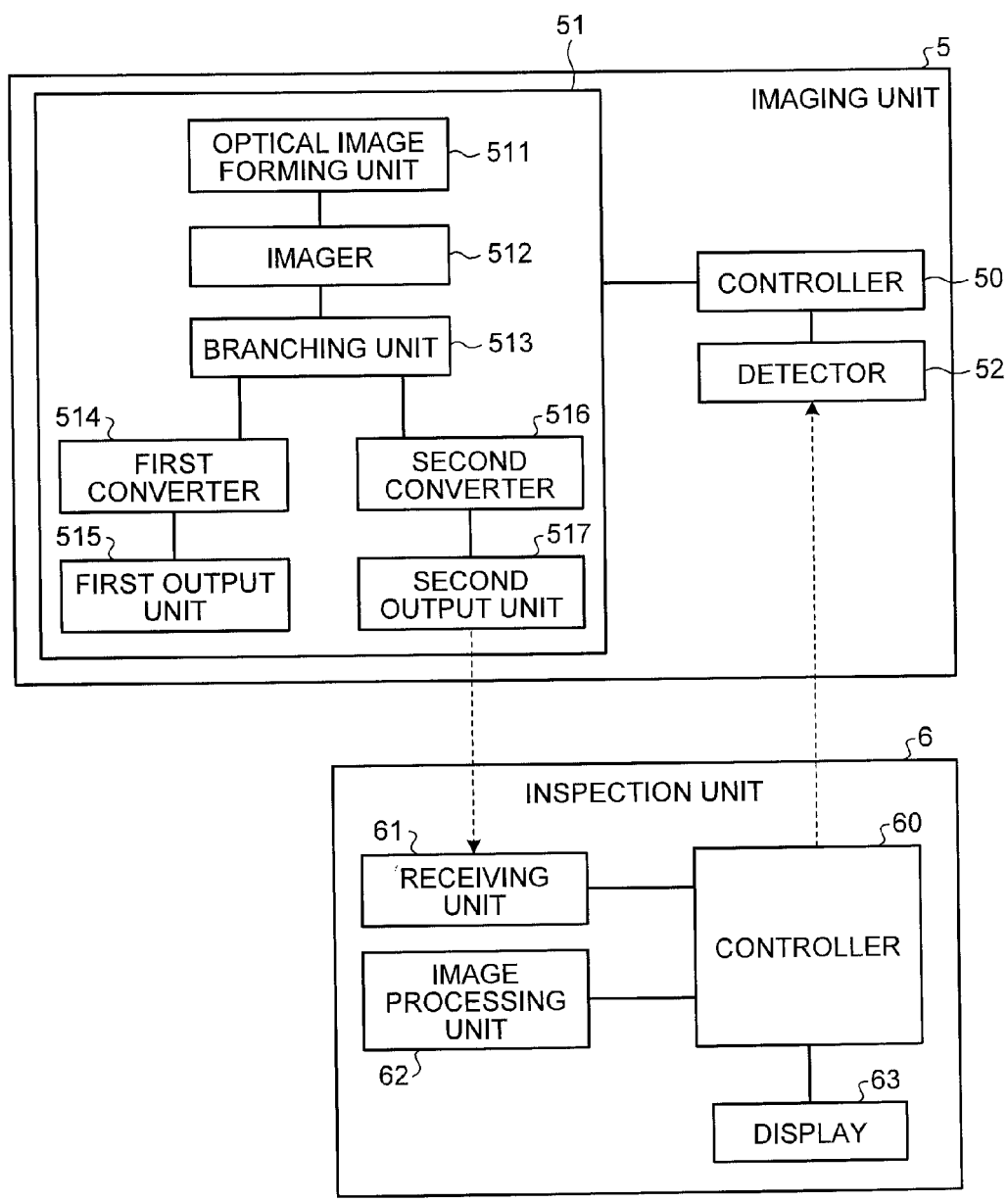
FIG. 3 is a block diagram illustrating the imaging unit mounted on the distal end portion of the endoscope apparatus, and an inspection unit, of the endoscope system according to the embodiment of the present invention.

FIG. 3 is a block diagram illustrating the imaging unit 5 mounted on the distal end portion 24 of the endoscope apparatus 2, and the inspection unit 6 for conduction inspection, of the endoscope system 1 according to this embodiment. The inspection unit 6 is able to supply electric power to the imaging element and inspects an output state of the imaging unit 5, and has: a controller 60 that controls the whole inspection unit 6; a receiving unit 61 (a second receiving unit) that receives from the imaging unit 5 the optical signal output from the imaging unit 5; an image processing unit 62 (second image processing unit) that processes the optical signal received by the receiving unit 61 and generates image information; and a display 63 that performs display of an image corresponding to the image information generated by the image processing unit 62.

If the imaging unit 5 (endoscope apparatus 2) is connected to the inspection unit 6 as illustrated in FIG. 3, the imaging unit 5 and the inspection unit 6 are communicatively connected by the second output unit 517 and the receiving unit 61. When this is done, the detector 52 acquires information on the unit being connected and outputs detection information of the connected unit to the controller 50. The controller 50 controls the branching unit 513, the first output unit 515, and the second output unit 517, based on the unit detection information acquired from the detector 52. That is, the controller 50 performs control to cause the first output unit 515 to output the optical signal if the unit detected by the detector 52 is the control unit 3 and to cause the second output unit 517 to output the electric signal if the detected unit is the inspection unit 6.

Based on the electric signal received by the receiving unit 61, the controller 60 causes the image processing unit 62 to process this electric signal and to generate image information, and based on this image information, causes the display 63 to display an image. Thereby, the observer is able to check the image displayed by the display 63 to determine whether or not there is abnormality in the image captured by the imager 512.

Since the signal converted by the second converter 516 is an electric signal including image information, an amount of information transmitted between the imaging unit 5 and the inspection unit 6 becomes less than an amount of information transmitted between the control unit 3 and the imaging unit 5. For example, an amount of information transmitted as an electric signal is about a few tenths to about a few hundredths of an amount of information transmitted as an optical signal. This means that signal transmission of a decreased amount of information as compared to that between the control unit 3 and imaging unit 5 is performed, but images for signals of different output modes are able to be checked. The optical fiber cable is used as a thing to transmit the optical signal between the receiving unit 31 and the first output unit 515, but since this optical fiber cable is made of glass, it is more easily affected by bending and twisting than a signal cable for electric signals and may be disconnected during observation. In contrast, a cable that transmits electric signals is able to be formed by using a material not easily affected by bending and twisting and thus disconnection or the like is hard to occur and more reliable signal transmission becomes possible.

As described above, the imaging unit 5 transmits the signal including the image information to the connected unit by changing the output route and output mode of the signal according to the connected unit. When that is done, if connected to the control unit 3, the imaging unit 5 outputs the optical signal converted by the first converter 514, and if connected to the inspection unit 6, the imaging unit 5 outputs the electric signal converted by the second converter 516. The imaging unit 5 connects communicatively to any one of the control unit 3 and the inspection unit 6.

Accordingly, if there is abnormality in an image acquired from the imaging unit 5, the observer is able to determine, by checking the image displayed on the respective displays 41 and 63, whether it is abnormality from an imager 512 and branching unit 513 side or abnormality from a first converter 514 and first output unit 515 side.

Further, if the imaging unit 5 is connected to the control unit 3, the controller 50 of the imaging unit 5 preferably makes the amount of information output by the second output unit 517 upon connection to the control unit 3 less than the amount of information output by the second output unit 517 upon connection to the inspection unit 6 and preferably makes an output of the second output unit 517 zero. Thereby, unnecessary output is able to be suppressed, and power consumption and heat generation due to electric conduction are able to be reduced.

According to the above described embodiment, a branching unit that branches a signal acquired by an imager and a plurality of output units connected to the branching unit are provided inside an imaging unit to change an output route according to a connected unit, and thus an abnormal part inside the imaging unit is able to be determined easily.

FIG. 4 is a block diagram illustrating a control unit 3a and an imaging unit 5a mounted on the distal end portion 24 of the endoscope apparatus 2, of an endoscope system according to a modified example of this embodiment. In the above described embodiment, the control unit 3 is described as being connected communicatively to one of the output units (first output unit 515) only, but like the control unit 3a according to the modified example, it may be connected communicatively to a plurality of output units.

The control unit 3a according to the modified example has: a controller 30a that controls the whole endoscope system including the imaging unit 5a; a first receiving unit 31a (first receiving unit), which is communicatively connected to the first output unit 515 of the imaging unit 5a and receives an optical signal output from the first output unit 515; a second receiving unit 31b (third receiving unit), which is communicatively connected to the second output unit 517 of the imaging unit 5 and receives an electric signal output from the second output unit 517; and an image processing unit 32a (first image processing unit), which processes a signal including image information received by the first receiving unit 31a or the second receiving unit 31b and generates image information of an image to be displayed by the display 41.

Further, the imaging unit 5a according to the modified example has a controller 50a that performs control of the above described image acquiring unit 51 and detector 52. Further, based on the unit detection information acquired from the detector 52, the controller 50a selects, from the first output unit 515 and second output unit 517, the output unit to output the signal to the unit to be connected, and performs control of outputting the signal from the selected output unit.

Like the above described modified example, also by selecting an output unit based on unit detection information to output a signal, it is possible to obtain the above described effects of the embodiment.

Further, in the above described modified example, it is possible to set the output unit that has become a non-output target into an off-state, and thereby, power consumption and heat generation due to electric conduction are able to be reduced.

The image processing unit 32a has been described as processing the signal including the image information received by the first receiving unit 31a or second receiving unit 31b, but it may have a plurality of image processing units, which are provided correspondingly to the first receiving unit 31a and second receiving unit 31b and individually perform processing of the signals respectively output by the first receiving unit 31a and second receiving unit 31b.

In the above described embodiment, the imaging unit mounted on the distal end portion of the treatment tool of the endoscope apparatus has been described as an example, but of course, application to electronic imaging units of various modes, such as digital cameras and digital video cameras, as well as portable telephones having imaging functions, is possible.

As described above, the imaging unit and imaging system according to the present invention are useful for easy determination of an abnormal part inside the imaging unit.

According to some embodiments, because a branching unit that branches a signal acquired by an imaging unit and a plurality of output units connected to the branching unit are provided inside an imaging unit to change an output route of a signal to outside according to a unit connected thereto, an abnormal part inside the imaging unit is able to be determined easily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit that is communicatively connected to a control unit for operation control, performs image capturing of a target to be captured under control of the control unit, and is also communicatively connected to an inspection unit for conduction inspection and subjected to the conduction inspection, the imaging unit comprising:
    an imager that has an imaging element configured to receive and photoelectrically convert light from the target to be captured;
    a branching unit configured to branch a signal including image information input from the imager into two signals;
    a first converter into which one of the two signals branched by the branching unit is input and which is configured to perform a conversion process of converting the input signal into an optical signal;
    a second converter into which the other of the two signals branched by the branching unit is input and which is configured to perform a conversion process of converting the input signal into an electric signal;
    a first output unit configured to output the optical signal converted by the first converter to outside;
    a second output unit configured to output the electric signal converted by the second converter to outside;
    a detector configured to detect a unit connected to the imaging unit; and
    a controller configured to cause the first output unit to output the optical signal if the unit detected by the detector is the control unit, and configured to cause the second output unit to output the electric signal if the unit detected by the detector is the inspection unit.

2. The imaging unit according to claim 1, wherein the detector detects connection of the control unit by detecting connection of an optical fiber cable.

3. The imaging unit according to claim 1, wherein the control unit performs control of making an amount of information output by the second output unit upon the connection to the control unit less than an amount of information output by the second output unit upon the connection to the inspection unit.

4. An imaging system, comprising:

the imaging unit according to claim 1;

the control unit that has a first receiving unit communicatively connected to the first output unit and configured to receive a signal from the imaging unit, and has a first image processing unit configured to generate image information based on the signal received by the first receiving unit;

the inspection unit that has a second receiving unit communicatively connected to the second output unit and configured to receive a signal from the imaging unit, and has a second image processing unit configured to generate image information based on the signal received by the second receiving unit; and a display configured to perform image display, based on the image information generated by the first image processing unit or the second image processing unit.

5. The imaging system according to claim 4, wherein the control unit further has a third receiving unit communicatively connected to the second output unit and configured to receive the signal from the imaging unit, and the first image processing unit generates the image information based on the signal received by the third receiving unit.

* * * * *